(12) United States Patent
Maestri et al.

(10) Patent No.: US 8,895,731 B2
(45) Date of Patent: Nov. 25, 2014

(54) TRIAZINE DERIVATIVES

(75) Inventors: Francesco Maestri, Bergamo (IT); Luca Bemporad, Bergamo (IT); Ferruccio Berte', Bergamo (IT)

(73) Assignee: 3V Sigma S.p.A., Milan (IT)

( * ) Notice: Subject to any disclaimer, the term of this patent is extended or adjusted under 35 U.S.C. 154(b) by 41 days.

(21) Appl. No.: 13/492,525

(22) Filed: Jun. 8, 2012

(65) Prior Publication Data
US 2013/0281692 A1    Oct. 24, 2013

(30) Foreign Application Priority Data

Apr. 18, 2012   (IT) .............................. MI2012A0644

(51) Int. Cl.
| | | |
|---|---|---|
| *C07D 251/54* | (2006.01) | |
| *C07D 251/42* | (2006.01) | |
| *C07D 413/12* | (2006.01) | |
| *A61K 8/49* | (2006.01) | |
| *A61Q 17/04* | (2006.01) | |

(52) U.S. Cl.
USPC ........... 544/196; 544/197; 544/198; 544/199; 252/405

(58) Field of Classification Search
USPC ............................ 544/197, 198, 199; 252/405
See application file for complete search history.

(56) References Cited

U.S. PATENT DOCUMENTS 5,346,691 A * 9/1994 Raspanti ......................... 424/59
5,744,127 A * 4/1998 Giuseppe et al. ............... 424/59

* cited by examiner

*Primary Examiner* — Venkataraman Balasubramanian
(74) *Attorney, Agent, or Firm* — Silvia Salvadori, P.C.

(57) ABSTRACT

The invention relates to novel intermediates for the preparation of substituted triazines used in particular in the cosmetic, detergent, coating, plastics and textile industries. The invention also relates to the processes for preparation of said intermediates and for the conversion of the latter into final products.

17 Claims, No Drawings

TRIAZINE DERIVATIVES

CROSS-REFERENCE TO RELATED APPLICATIONS

This application claims priority to and the benefit of Italian Application No. MI2012A000644 filed on Apr. 18, 2012, the content of which is incorporated herein by reference in its entirety.

The present invention relates to novel derivatives of symmetrical triazine and their use as intermediates for the production of substituted triazines used in particular in the cosmetic, detergent, coating, plastics and textile industries.

The invention also relates to the preparation process of said intermediates.

PRIOR ART

Numerous derivatives of symmetrical triazine are known which can be used in a number of technical applications and sectors due to their properties of absorbing UV rays, in particular UV-A and UV-B rays.

Examples of these triazines are disclosed in U.S. Pat. No. 4,617,390, U.S. Pat. No. 4,724,137, U.S. Pat. No. 5,233,040, U.S. Pat. No. 5,252,323, U.S. Pat. No. 5,332,568, U.S. Pat. No. 5,346,691, U.S. Pat. No. 5,393,517, U.S. Pat. No. 5,744,127, U.S. Pat. No. 5,759,525, U.S. Pat. No. 5,801,244, U.S. Pat. No. 6,018,044, U.S. Pat. No. 6,193,960, US 2002085981 and US 2005143577.

The structural characteristics of the triazines currently available are the presence of three substituents on the triazine ring which may be alkylamine, alkylphenylamine, alkyamidophenylamine, alkyloxycarbonylphenylamine or heteroarylphenylamine.

The known processes for the preparation of this type of tri-substituted 1,3,5-triazine involve the introduction of substituents onto the triazine ring in a suitable sequence by reacting a cyanuryl halide, generally cyanuryl chloride, with suitable pre-prepared amines.

The processes described, particularly those wherein the three substituents are not all equal, suffer from some drawbacks associated with the large number of steps involved and the need to purify the various intermediates often in order to guarantee satisfactory purity of the final product.

The overall efficiency of the process is therefore affected, with adverse effects on the costs of production.

Moreover, the products obtained may present characteristics which are less than ideal in terms of purity and of other properties that are important for their use, such as colour, odour and stability.

The preparation scheme of a triazine disclosed in U.S. Pat. No. 5,346,691, available on the market under the UVASORB HEB® brand, is shown below by way of example.

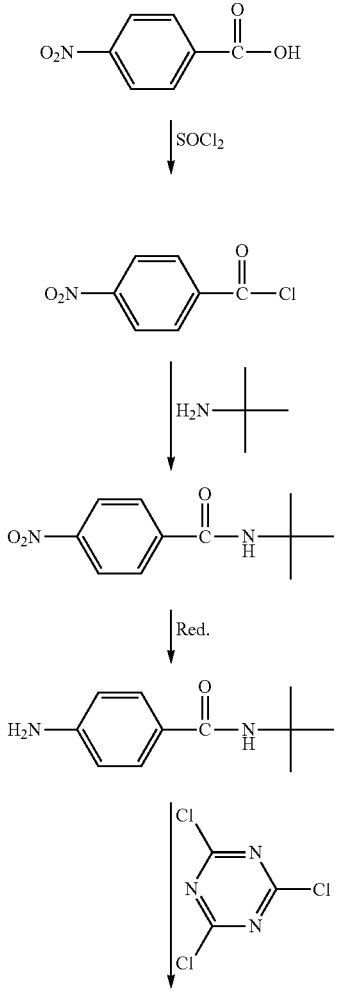

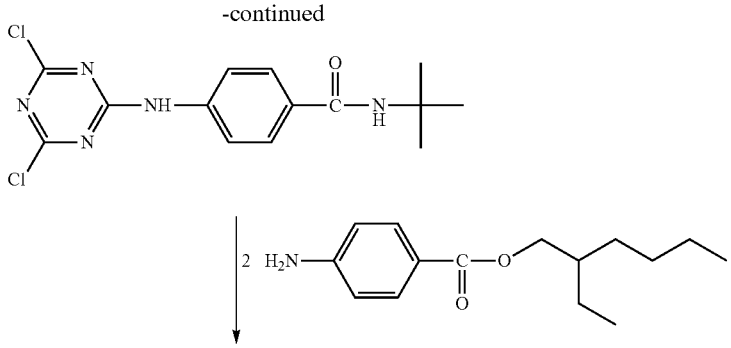

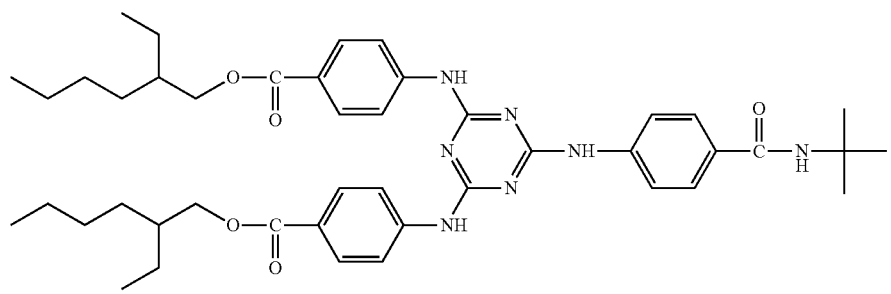

There is consequently a need for processes which do not present these drawbacks, and in particular allow the preparation of triazines with high purity at high yields and low cost.

DESCRIPTION OF THE INVENTION

It has now been found that triazine derivatives such as those mentioned above can be advantageously obtained from novel intermediates, which in turn are obtainable by innovative, advantageous synthesis processes.

The object of the invention is therefore the novel intermediates, their preparation processes, and their use for the synthesis of triazine derivatives with substituents which are different or all equal.

The intermediates of the present invention have the following formula (I):

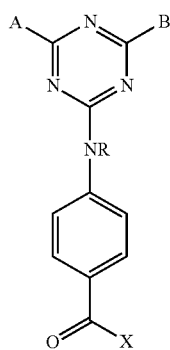

I wherein A and B, which are the same or different, represent an $NR_1R_2$ group or a group of formula II:

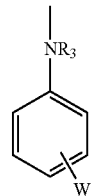

II wherein group W can be an alkyl, isoalkyl, cycloalkyl, aryl, hydroxyl, alkoxy, halogen, nitro, nitrile, sulphonic, —COX, —COOR4, or —CONR5R6 group, or a group of formula III or IV

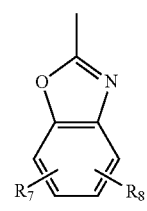

III

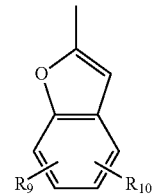

IV

X is a leaving group, preferably a halogen or mesyl, tosyl or similar groups;

groups R—R10, which are the same or different, represent hydrogen, straight or branched C1-C12 alkyl and C3-C6 cycloalkyl, and groups R1 and R2, or R5 and R6, together with the nitrogen atom they are linked to, can also form a morpholino ring;

with the proviso that A and B cannot simultaneously be a group of formula II with W=—COX.

R4, R5 and R6 can also be polyalkylene-polysiloxane groups, such as —(CH$_2$)n-Sil, where Sil is a polysiloxane group;

A and B, which are the same or different, are preferably groups NR1R2 or the groups of formula V, VI, VII, VIII and IX:

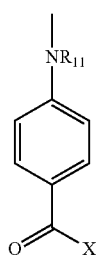

V

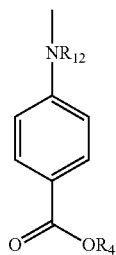

VI

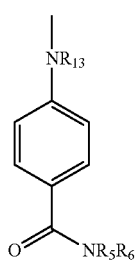

VII

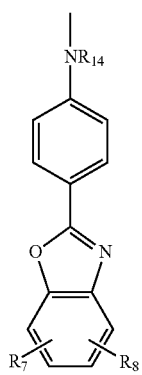

VIII

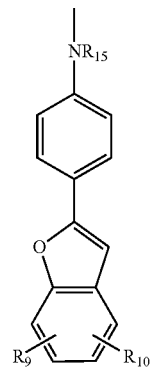

IX wherein groups X, R—R10, which are the same or different, independently of one another, acquire the values previously defined, and groups R11-R15 are also H, alkyls and cycloalkyls, which are the same or different independently of one another, with the proviso that A and B cannot simultaneously be a group of formula V.

In compounds of formula I, X is preferably halogen, more preferably chlorine, one of R1 and R2 is hydrogen, and the other is a straight or branched alkyl having 1 to 12 carbon atoms, preferably 2-ethylhexyl; R11-R15 are preferably hydrogen, and R4 is preferably a straight or branched alkyl group having 1 to 12 carbon atoms, such as 2-ethylhexyl.

One of R5 or R6 is preferably hydrogen and the other is a C1-C12 alkyl group, such as tert-butyl.

R7-R10 are preferably hydrogen, or one is hydrogen and the other is a C1-C12 alkyl, such as tert-amyl.

A and B are preferably two equal groups, with the proviso that one of them is not a group of formula V.

Preferred examples of the compounds according to the invention have the following formulas:

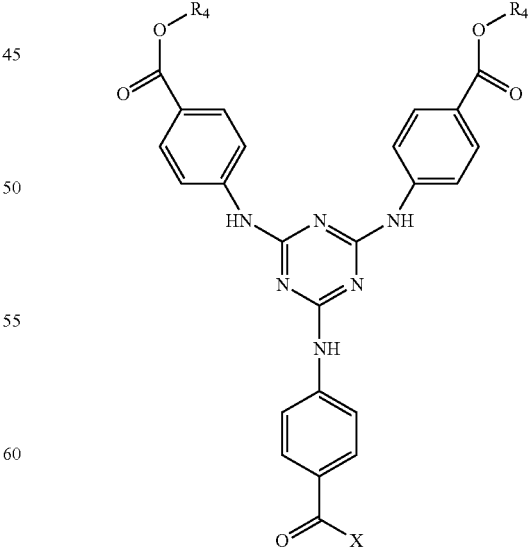

wherein X is as defined above and R4 is C1-C12 alkyl, X is preferably chlorine, and R4 is 2-ethylhexyl;

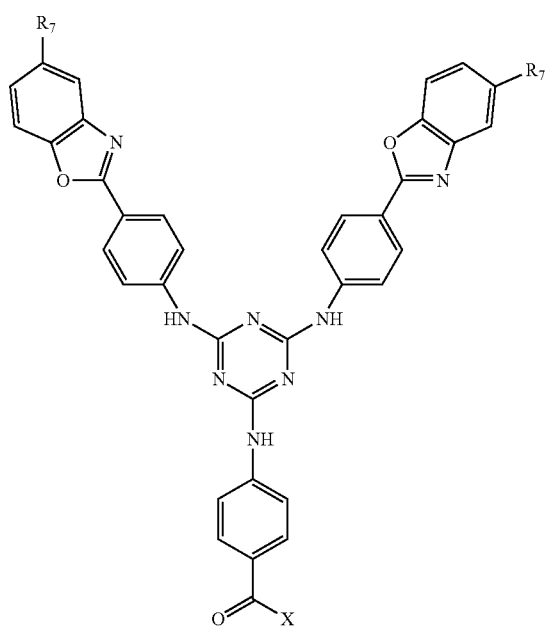

wherein X is as defined above, R7 are C1-C12 alkyl or isoalkyl groups,

X is preferably chlorine and R7 are tert-amyl groups;

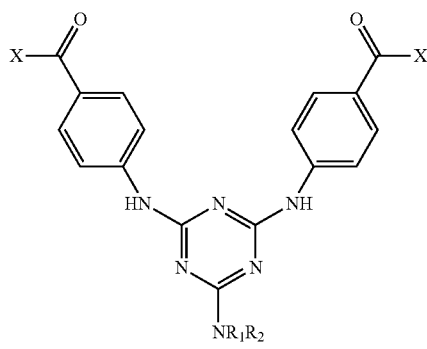

wherein X is as defined above, R1 is hydrogen and R2 is alkyl or isoC1-C12 alkyl, R2 is preferably 2-ethylhexyl and X is chlorine;

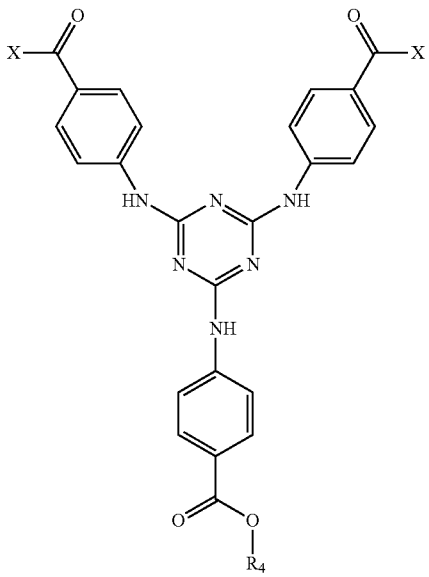

wherein X is as defined above, R4 is alkyl or isoC1-C12 alkyl, R4 is preferably 2-ethylhexyl and X is chlorine;

wherein X is as defined above, R5 is hydrogen, R6 is alkyl or isoC1-C12 alkyl, R6 is preferably tert-butyl and X is chlorine.

The intermediates of formula I wherein A and B are not groups of formula V can be advantageously converted to the final triazines as follows:

A)
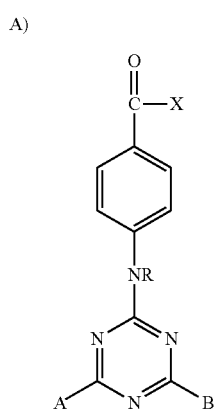
B)
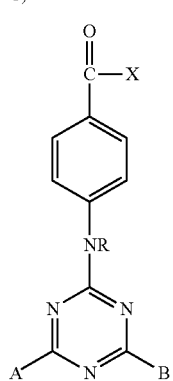
C)
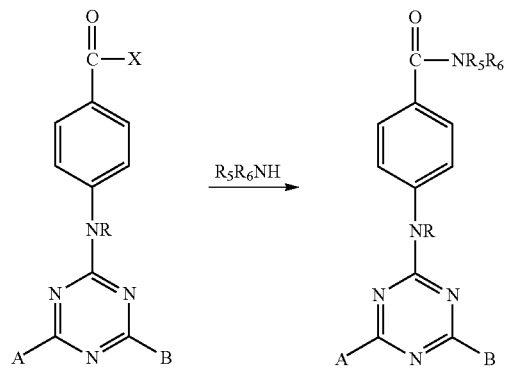
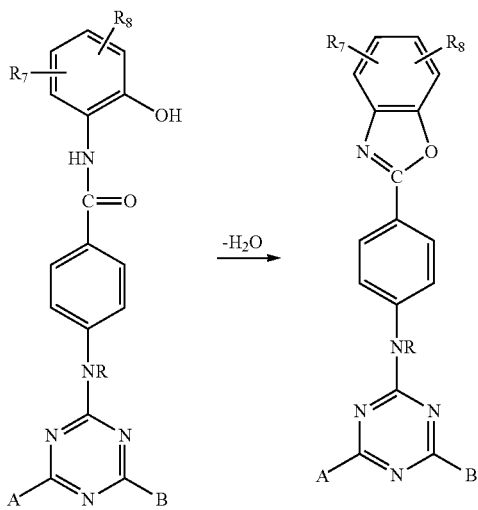
wherein the groups R, R4, R5, R6, R7, R8, A, B and X are as defined above.
The intermediates of formula I wherein A is not a group of formula V and B is a group of formula V can be advantageously converted to the final triazines according to the following scheme:
A)
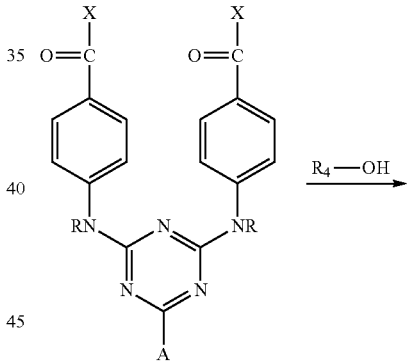
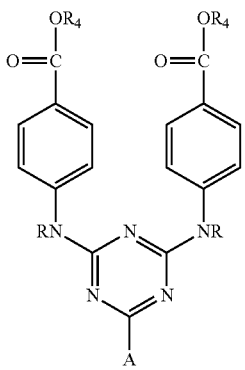

B)

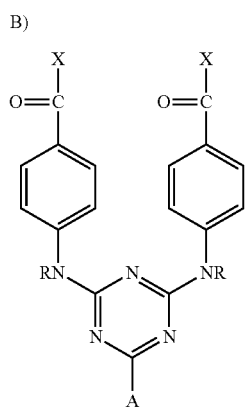

C)

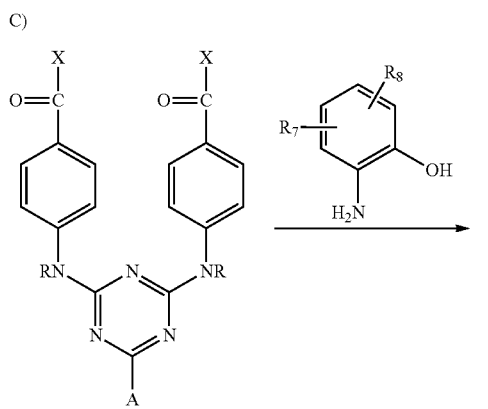

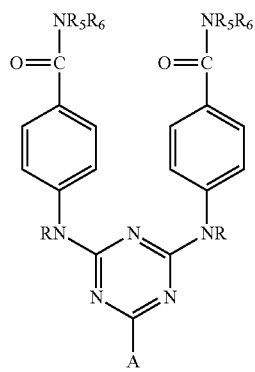

wherein groups R, R4, R5, R6, R7, R8, A and X are as defined above.

As will be seen from the above schemes, although the intermediate compounds according to the present invention are particularly suitable to obtain triazine with different substituents, they also enable triazine wherein the three substituents are all equal to be obtained where required.

The invention also relates to processes for preparation of the compounds of formula I.

The compounds of formula I wherein A and B are not groups of formula V can be prepared by the process illustrated in the scheme below, wherein Z is chlorine or bromine, R, A, B and X are as defined above, and n is 2, 3 or 5, Y is SO, $SO_2$, P, PO, CO, $(CO)_2$:

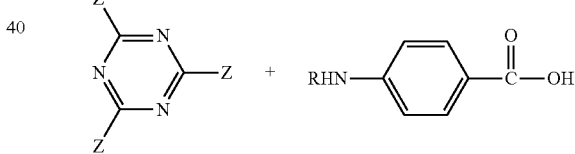

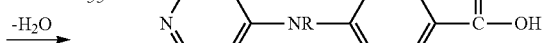

-continued

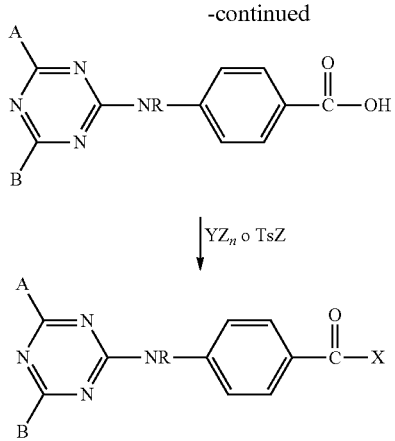

The process comprises:

a) reacting cyanuryl chloride or bromide with one equivalent of a compound of formula:

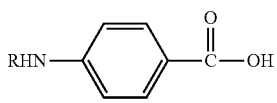

wherein R is as defined above;
to give a compound of formula:

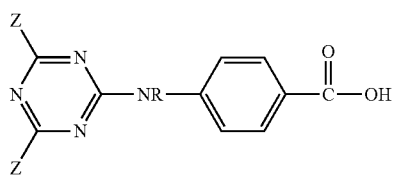

or a metal salt thereof, such as an alkali metal salt like sodium, wherein

Z is chlorine or bromine and R is as defined above, R is preferably H and Z is chlorine;

b) reacting the compound obtained in a) with two equivalents of compounds of formula AH and/or BH wherein A and B are as defined above, excluding the group of formula V, to give a compound of formula:

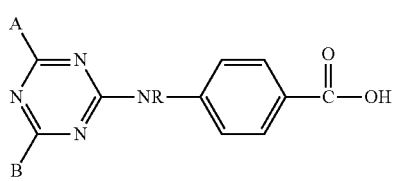

or a metal salt thereof, such as an alkali metal salt like sodium, wherein A, B and R are as defined above;

c) reacting the compound obtained in b) with agents selected from halogenating agents such as thionyl chloride, sulphuryl chloride, phosphorus trichloride, phosphorus pentachloride, phosphorus oxychloride, oxalyl chloride, phosgene, or mesyl or tosyl halides.

Alternatively, the order of steps a) and b) can be reversed, reacting the cyanuryl halide first with two equivalents of compounds AH and BH and then with one equivalent of the compound of formula

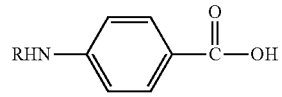

The reaction between cyanuryl halide and the compound of formula

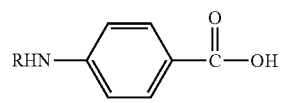

is conducted in a solvent, in the presence of a base which can be added at a later stage, so as to promote the formation of the product of monosubstitution.

The preferred solvents are all solvents compatible with the reagents, in particular ketones such as acetone, methyl ethyl ketone, methyl isobutyl ketone and diisobutylketone, aromatic hydrocarbons such as benzene, toluene and xylene, saturated hydrocarbons such as pentane, hexane, cyclohexane, heptane, octane, isooctane, decane and isoparaffin, halogenated solvents such as methylene chloride, chloroform, dichloroethane and trichloroethane, ethers such as diethylether, tetrahydrofuran and dioxane, esters such as methyl acetate and ethyl acetate, nitriles such as acetonitrile, and alcohols such as isopropanol and tert-butanol. More preferred solvents are ketones, acetone being particularly preferred. Said solvents are preferably anhydrous, but can also contain small amounts of water.

Suitable bases are oxides, hydroxides, alkaline or alkaline earth carbonates or bicarbonates, preferably sodium hydroxide, sodium carbonate and sodium or potassium bicarbonate or tertiary amines, preferably trimethylamine, triethylamine or pyridine.

The reaction can be conducted at temperatures between $-30°$ C. and $60°$ C., preferably between $-20°$ C. and $30°$ C., and even more preferably between $-10°$ C. and $10°$ C., and at pressures of between 0.01 bar and 10 bar, preferably between 0.1 bar and 2 bar, and even more preferably between 0.5 and 1.5 bar.

The stage b) reactions are preferably conducted in a solvent compatible with the reagents, but in some cases the solvent function can be performed by an adequate excess of the reagent.

The preferred solvents are all solvents compatible with the reagents, in particular ketones such as acetone, methyl ethyl ketone, methyl isobutyl ketone and diisobutylketone, aromatic hydrocarbons such as benzene, toluene and xylene, saturated hydrocarbons such as pentane, hexane, cyclohexane, heptane, octane, isooctane, decane and isoparaffin, halogenated solvents such as methylene chloride, chloroform, dichloroethane and trichloroethane, ethers such as diethylether, tetrahydrofuran and dioxane, esters such as methyl acetate and ethyl acetate, nitriles such as acetonitrile, and alcohols such as isopropanol and tert-butanol. More preferred solvents are aromatic hydrocarbons, toluene and xylene being particularly preferred.

Said solvents are preferably anhydrous, but can also contain small amounts of water.

The reaction can be conducted in the presence of a base, which can also be added at a later stage. Suitable bases are oxides, hydroxides, alkaline or alkaline earth carbonates or bicarbonates, preferably sodium hydroxide, sodium carbonate and sodium or potassium bicarbonate or tertiary amines, preferably trimethylamine, triethylamine or pyridine.

The reaction can be conducted at temperatures between 10° C. and 220° C., preferably between 30° C. and 200° C. and even more preferably between 50° C. and 160° C., and at pressures of between 0.01 bar and 10 bar, preferably between 0.1 bar and 2 bar, and even more preferably between 0.5 and 1.5 bar.

Finally, the carboxy group can be converted to the COX group (stage c) by known organic chemistry methods (A. I. Vogel, "Chimica organica pratica", Casa Editrice Ambrosiana, 3rd edition, 1967; M. B. Smith and J. March, "March's Advanced Organic Chemistry", Wiley, 6th edition, 2007), preferably by treatment with thionyl chloride, sulphuryl chloride, phosphorus trichloride, phosphorus pentachloride, phosphorus oxychloride, oxalyl chloride, phosgene, and even more preferably with thionyl chloride.

The reaction can be conducted in the presence of a solvent, but in some cases the solvent function can be performed by an adequate excess of the halogenating agent.

The preferred solvents are all solvents compatible with the reagents and with the product of reaction, and in particular with the halogenating agent and the COX group which is synthesised. Aromatic hydrocarbons such as benzene, toluene and xylene, saturated hydrocarbons such as pentane, hexane, cyclohexane, heptane, octane, isooctane, decane and isoparaffin, halogenated solvents such as methylene chloride, chloroform, dichloroethane and trichloroethane, ethers such as diethylether, tetrahydrofuran and dioxane, esters such as methyl acetate and ethyl acetate, nitriles such as acetonitrile, and ketones, can be used in particular. The preferred solvent is an aromatic hydrocarbon, in particular toluene or xylene, more preferably xylene. The same solvent as used for stage b) is preferably used.

The reaction can be conducted at temperatures between 10° C. and 150° C., preferably between 30° C. and 100° C. and even more preferably between 50° C. and 80° C., and at pressures of between 0.01 bar and 10 bar, preferably between 0.1 bar and 2 bar, and even more preferably between 0.5 and 1.5 bar.

The compounds of formula I wherein A is not a group of formula V and B is a group of formula V can be prepared in accordance with the following synthesis scheme, wherein Z is chlorine or bromine, R, A and X are as defined above, n is 2, 3, or 5, and Y is SO, SO$_2$, P, PO, CO, (CO)$_2$:

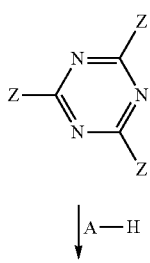

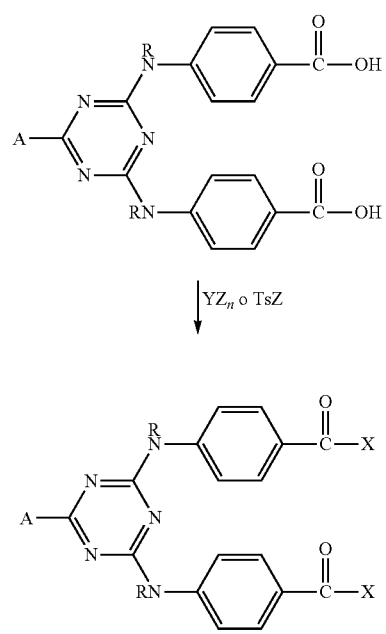

which comprises:

a) reacting cyanuryl chloride or bromide with one equivalent of a compound of formula AH to give a compound of formula:

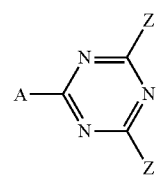

wherein Z is chlorine or bromine, A is as defined above, and Z is preferably chlorine;

b) reacting the compound obtained in a) with two equivalents of a compound of formula:

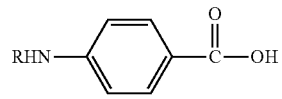

wherein R is as defined above and R is preferably H;
to give a compound of formula:

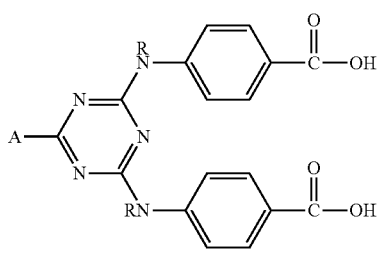

or a metal salt thereof, such as an alkali metal salt like sodium, wherein R and A are as defined above;

c) reacting the compound obtained in b) with agents selected from halogenating agents such as thionyl chloride, sulphuryl chloride, phosphorus trichloride, phosphorus pentachloride, phosphorus oxychloride, oxalyl chloride, phosgene, or mesyl or tosyl halides.

The solvents and reaction conditions are identical or substantially similar to those of the corresponding stages of reaction described above for the first synthesis scheme. Once again, the order of steps a) and b) can be reversed, reacting the cyanuryl halide first with two equivalents of the para-aminobenzoic acid derivative and then with AH and BH.

The products of formula I wherein A and B are not groups of formula V or A is not a group of formula V and B is a group of formula V are versatile intermediates for the preparation of variously substituted triazines by classic reactions well-known in organic chemistry (A. I. Vogel, "Chimica organica pratica", Casa Editrice Ambrosiana, 3rd edition, 1967; M. B. Smith and J. March, "March's Advanced Organic Chemistry", Wiley, 6th edition, 2007), wherein carbonyl groups activated with a leaving group are reacted with alcohols to give the corresponding esters, or with primary and secondary amines to give the corresponding amides.

The processes of converting the products of formula I into the corresponding esters and amides also fall within the scope of the present invention.

Reactions of converting an alcohol to an ester can be conducted in an excess of the same alcohol, which performs the function of both reagent and solvent, or in the presence of a solvent.

Similarly, reactions of conversion to an amide can be conducted in an excess of amine, which performs the function of reagent, solvent and base to neutralise the acidity it releases. Alternatively, the reaction can be conducted in the presence of a solvent.

The preferred solvents are all solvents compatible with the reagents, and in particular with the COX group. Aromatic hydrocarbons such as benzene, toluene and xylene, saturated hydrocarbons such as pentane, hexane, cyclohexane, heptane, octane, isooctane, decane and isoparaffin, halogenated solvents such as methylene chloride, chloroform, dichloroethane and trichloroethane, ethers such as diethylether, tetrahydrofuran and dioxane, esters such as methyl acetate and ethyl acetate, nitriles such as acetonitrile, and ketones, can be used in particular. The preferred solvent is an aromatic hydrocarbon, in particular toluene or xylene, more preferably xylene. The same solvent as used for stage c) is preferably used.

The reaction can be conducted at temperatures between 10° C. and 200° C., preferably between 30° C. and 150° C. and even more preferably between 50° C. and 100° C., and at pressures of between 0.01 bar and 10 bar, preferably between 0.1 bar and 2 bar, and even more preferably between 0.5 and 1.5 bar.

The reaction can be conducted in the presence of a base, which can also be added at a later stage, designed to neutralise the acid groups released during the reaction.

Suitable bases are oxides, hydroxides, alkaline or alkaline earth carbonates or bicarbonates, preferably sodium hydroxide, sodium carbonate and sodium or potassium bicarbonate or tertiary amines, preferably trimethylamine, triethylamine or pyridine.

A particular case of reaction of the compounds of formula I with amines relates to the use of o-aminophenols, possibly mono- or di-alkylsubstituted on the aromatic ring, to give the corresponding amides. The latter can be further modified by anhydration, giving rise to cyclisation reactions with the formation of the corresponding benzoxazole groups. The reaction is promoted by the presence of acid catalysts such as hydrochloric acid, sulphuric acid, methanesulphonic acid and p-toluenesulphonic acid, and by the removal from the reaction environment of the water released during the reaction. The reaction can be performed in the absence or presence of a compatible solvent. The preferred solvents are aromatic and saturated hydrocarbons, and even more preferably toluene and xylene. Typical reaction temperatures are those between 80° C. and 200° C., preferably between 100° C. and 180° C., even more preferably between 120° C. and 160° C., and pressures of between 0.01 bar and 10 bar, preferably between 0.1 bar and 2 bar, and even more preferably between 0.5 and 1.5 bar.

Processes of conversion of the compounds of formula I by reaction with aminophenols to give amides, and consequently benzoxazole groups, are also part of the present invention.

The compounds of formula I can also be converted to other products by reaction with compounds containing functions able to react with the COX groups as defined above.

The processes according to the invention are advantageous because they can also be performed using a single solvent, and with no need to isolate and/or purify the intermediates. Solvents of a different nature can also be used if necessary, and isolations and intermediate purifications can optionally be introduced. Unlike known methods, wherein the alkoxycarbonylphenylamine, alkylamidophenylamine or heteroarylphenylamine functions are introduced onto the triazine ring at an early stage of synthesis, the processes according to the invention consist of a smaller number of steps, and are therefore more efficient.

Moreover, the final products obtainable by reacting the intermediates of formula I are purer and possess better colour characteristics, which are particularly important for specific uses.

The invention is illustrated in greater detail in the examples below.

Example 1

Synthesis of 4-((4,6-bischloro-1,3,5-triazin-2-yl)amino)-benzoic acid 75.0 g of cyanuryl chloride, 37.3 g of sodium bicarbonate and 304 g of anhydrous acetone, precooled to −10° C., were loaded into a 2-liter flask fitted with a stirrer, thermometer, condenser and dropping funnel.

A solution, precooled to −10° C., consisting of 54.7 g of p-aminobenzoic acid and 523 g of anhydrous acetone, was added in 45 min, under stirring at −10° C.

After 60 minutes' stirring at −10° C., 100 g of demi water, precooled to 0-2° C., was added in approx. 15 minutes. After two more hours of completion at −10° C. the product, in the form of a white solid in suspension, was isolated by filtration under vacuum. The wet filtration panel was then washed in sequence, first with aqueous acetone and then with anhydrous acetone. The wet panel was stove-dried under vacuum to obtain 139 g of fine white powder, consisting of a mixture of the desired product and inorganic salts. The powder was analysed, determining an active chlorine content of 19.8% w/w as the difference between total chlorine (29.4% w/w) and free chlorides (9.6% w/w). The product was also characterised by UPLC-MS chromatography.

Example 2

Synthesis of 4-(4,6-bis(4-((2-ethylhexyloxy)carbonyl)-phenylamine)-1,3,5-triazin-2-ylamino)benzoic] acid 568 g of anhydrous xylene and 139.0 g of the product prepared in example 1 were loaded into a 2-liter flask fitted with a stirrer, thermometer, dropping funnel and condenser.

645 g of a 30% xylene solution of 2-ethyl hexyl 4-aminobenzoate was added in 30 minutes to the mixture, stirred at 90° C. When the addition had been completed, the mixture was maintained at 90° C. for 15 min and then heated to 125° C. in 60 minutes, obtaining a thick whitish suspension. The mixture was maintained under stirring at 125° C. for 3 hours, during which time a gradual reduction in the development of hydrochloric acid and an increase in the fluidity of the mixture was observed. After cooling to 80-90° C., 280 g of 15% aqueous sodium carbonate was added cautiously. After 30 minutes' mixing at 70-80° C., stirring was interrupted and the underlying alkaline aqueous phase was discharged. After two further aqueous washes, the residual water was removed by azeotropic distillation under atmospheric pressure, followed by distillation of xylene to concentrate the solution.

680 g of whitish dispersion was obtained, containing approx. 275 g of the desired product, which was characterised by UPLC-MS. The dispersion "as is" was used for the subsequent stages of synthesis.

Example 3

Synthesis of 4-(4,6-bis(4-((2-ethylhexyloxy)-carbonyl)-phenylamine)-1,3,5-triazin-2-ylamino)benzoyl chloride)

62.4 g of thionyl chloride, 31.2 g of anhydrous xylene and 0.22 g of dimethylformamide were loaded into a 1-liter flask fitted with a stirrer, thermometer, condenser and dropping funnel. 220 g of the final dispersion obtained in example 2 was fed in 3 hours into the well-stirred mixture, maintained at 70° C.

The hydrochloric acid and sulphur trioxide released during dripping were removed by bubbling in an aqueous solution of sodium hydroxide. When the addition had been completed, the mixture was stirred at 70° C. for a further 2 hours. The excess thionyl chloride was then removed by distillation under vacuum, and the excess xylene as distillation tail. 235 g of xylene mixture, containing approx. 89 g of the desired acyl chloride, remained in the flask. The mixture "as is" was used for the successive functionalisation reactions, to give a variety of triazine derivatives. A sample of acyl chloride was isolated for characterisation by complete removal of the solvent. The acyl chloride was reacted with an excess of methanol to obtain the corresponding methyl ester, the structure of which was confirmed by IR, NMR and UPLC-MS analysis.

Example 4

Synthesis of benzoic acid, 4,4'-[[6-[[4-[[(1,1-dimethyl-ethyl)amino]carbonyl]phenyl]amino-1,3,5-triazin-2,4-diyl]diimino]bis-,-bis(2-ethylhexyl) ester 36.5 g of tert-butylamine was added under stirring, in 15 minutes, to 235 g of the xylene mixture obtained in example 3, maintained at 30-40° C. by cooling. After a further 30 minutes at 40° C., the mixture was heated to 95° C. in 60 minutes.

After 60 minutes at 95° C. the temperature was reduced to 50-60° C., and 212 g of 12.5% w/w sodium carbonate was added under stirring.

After 15 minutes at 50° C., stirring was interrupted, and the underlying alkaline aqueous phase was discharged after separation. The organic phase was washed with water. After removal of the residual water by azeotropic distillation in the presence of a filtrating earth, the mixture was cooled to 60° C. and filtered hot.

The product was then isolated by complete removal of the xylene by distillation under vacuum. The molten product thus obtained was flaked and ground, obtaining 95 g of a whitish powder with a chromatographic purity of 98.65%, Apha colour (10% w/v in toluene)=189, softening point 90-120° C. and extinction E'=1522 at 311 nm. The structure of the product was confirmed by IR, NMR and UPLC-MS analysis.

Example 5

Synthesis of tris(2-ethylhexyl)-4,4',4''-(1,3,5-triazine-2,4,6-triyltriimino)tribenzoate Similarly to the process reported in example 4, the dispersion obtained according to example 3 was reacted with an excess of 2-ethyl-1-hexyl alcohol. Alkaline washes were performed at the end of the reaction. The excess alcohol and xylene were completely removed by distillation under vacuum, obtaining a molten product that was flaked and ground. The desired symmetrically substituted triazine was thus obtained as a white powder with a melting point of 128° C. and extinction E'=1541 at 314 nm. The structure was confirmed by IR and NMR analysis.

Example 6

Synthesis of 2,4-bis-[4-[5-(1,1-dimethylpropyl)benzoxazol-2-yl]phenylimino]-6-(2-ethylhexyl)imino-1,3,5-triazine Similarly to the process reported in example 1, the cyanuryl chloride was reacted with 2-ethyl-1-hexylamine, to obtain the corresponding intermediate 2,4-bischloro-6-(2-ethylhexyl)imino-1,3,5-triazine. Similarly to the process reported in examples 2 and 3, the latter was reacted with two equivalents of p-aminobenzoic acid to give the corresponding diacid, which was then converted to the corresponding diacyl chloride by the action of thionyl chloride.

The intermediate was then reacted with two equivalents of o-amino-p-tert-amylphenol to obtain the corresponding diamide. Dehydration and consequent cyclisation was induced by heating at approx. 170° C. with acid catalysis, giving rise to the formation of the desired substituted triazine, bearing two benzoxazole residues. The solid product has a melting point of 126° C. and extinction E'=1410 at 339 nm. The structure was confirmed by IR and NMR analysis.

Examples 7-10

Synthesis of Other Triazines from the Acyl Chloride Obtained in Example 3

The acyl chloride obtained according to example 3 was used to prepare the triazines of formula X described in the table below. In particular, example 7 describes the product obtained by the procedure described in example 5, by reacting acyl chloride with cyclohexyl alcohol instead of 2-ethyl-1-hexyl alcohol. Examples 8-10 report the products obtained according to the method described in example 6, by reacting the acyl chloride with substituted di-aminophenols to give the corresponding amide, which by cyclisation with acid catalysis led to the variously substituted mono-benzoxazole derivatives

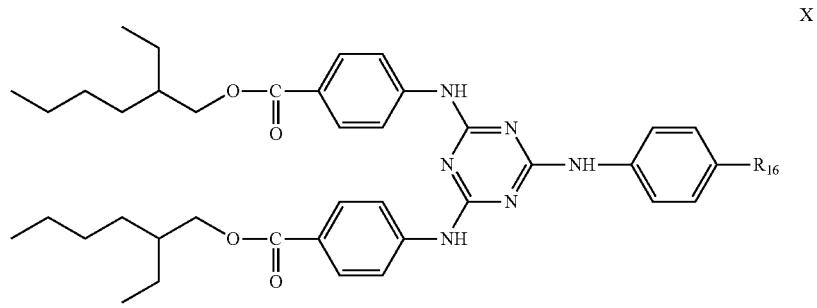

X as described in the table below.

Examples 11-18

Synthesis of Other Triazines Disubstituted with Benzoxazole Groups

Similarly to the process reported in example 6, variously substituted compounds of formula XI

TABLE 1

| Example | R16 | m.p. (° C.) | $E_1^1$ | nm |
|---|---|---|---|---|
| 7 | —C(=O)—O—cyclohexyl | 144-147 | 1615 | 313 |
| 8 | benzoxazol-2-yl | 104-104 | 1373 | 314 |
| 9 | 5-methyl-benzoxazol-2-yl | 162-193 | 1318 | 314 |
| 10 | 5-tert-butyl-benzoxazol-2-yl | 121-123 | 1257 | 314 | were prepared. An amine selected from tert-octylamine, 2-ethylhexyl p-aminobenzoate or N-tert-butyl-p-aminobenzamide was used in the first step instead of 2-ethyl-1-hexylamine. After obtaining the corresponding diacyl chlorides with similar steps to those reported in example 6, they were reacted with o-aminophenol or alkylsubstituted o-aminophenols to give the corresponding amides which, after cyclisation in the presence of acid catalysis, supplied the corresponding products bearing two benzoxazole groups, summarised in the table below.

TABLE 2

| Example | R17 | R18 | m.p. (° C.) | $E_1^1$ | nm |
|---|---|---|---|---|---|
| 11 | H | (2-ethylhexyl 4-methylbenzoate) | 215-217 | 1594 | 337 |
| 12 | tert-butyl | (2-ethylhexyl 4-methylbenzoate) | 187-190 | 1333 | 337 |
| 13 | tert-butyl | (N-tert-butyl-4-methylbenzamide) | >250 | 1479 | 337 |
| 14 | H | (N-tert-butyl-4-methylbenzamide) | 191-194 | 1631 | 336 |
| 15 | H₃C— | (N-tert-butyl-4-methylbenzamide) | >250 | 1548 | 337 |
| 16 | tert-butyl | (2,4,4-trimethylpentan-2-yl) | 143-145 | 1433 | 338 |
| 17 | H | (2,4,4-trimethylpentan-2-yl) | 196-198 | 1594 | 337 |
| 18 | H₃C— | (2,4,4-trimethylpentan-2-yl) | 232-233 | 1562 | 338 |

The invention claimed is:

1. Compound of formula I

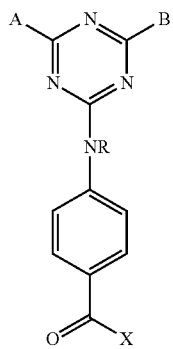

wherein A and B, which can be the same or different, are an NR1R2 group, or a group of formula II:

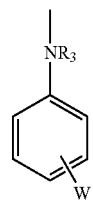

wherein group W can be an alkyl, isoalkyl, cycloalkyl, aryl, alkoxy, halogen, nitro, nitrile, COX, —COOR4, or —CONR5R6 group or a group of formula III or IV

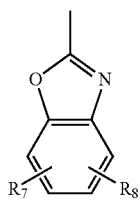

III

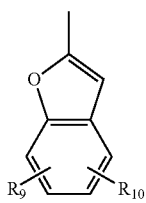

IV

X is a halogen;
groups R—R10, which can be the same or different, are hydrogen, straight or branched C1-C12 alkyl, C3-C6 cycloalkyl, R1 and R2, or R5 and R6, and together with the nitrogen atom they are linked to, can also form a morpholino ring;
with the proviso that A and B cannot be at the same time a group of formula II with W=-COX,
R4, R5 and R6 can also be polyalkylene-polysiloxane groups, with the proviso that in the group COOR4, R4 cannot be hydrogen.

2. Compound of formula I according to claim 1 wherein A and B, which can be the same or different, are an NR1R2 group, or one of the groups of formula V, VI, VII, VIII and IX

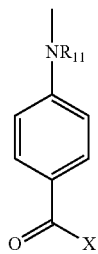

V

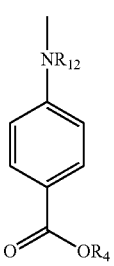

VI

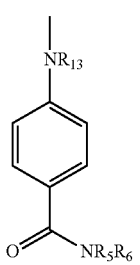

VII

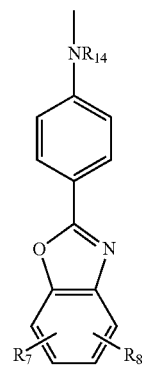

VIII

IX wherein the X, R—R10 groups, which can be independently the same or different, have the meanings defined above, and the R11-R15 groups are also H, alkyls and cycloalkyls which can be independently the same or different,
with the proviso that A and B cannot be at the same time a group of formula V.

3. Compound according to claim 2 wherein R1 is H and R2 is straight or branched C1-C12 alkyl, C3-C6 cycloalkyl.

4. Compound according to claim 1 wherein A is a group of formula V.

5. Compound according to claim 1 wherein A and B are the same, with the exclusion of the groups of formula V.

6. Compound according to claim 2, wherein X is chlorine, wherein R1 is H and R2 is straight or branched alkyl having 1 to 12 carbon atoms, R11-R15 are hydrogen, R4 is a straight or branched alkyl group having 1 to 12 carbon atoms, either R5 or R6 is hydrogen and the other is a C1-C12 alkyl group, and R7-R10 are hydrogen or one is hydrogen and the other is a C1-C12 alkyl.

7. Compound according to claim 1 selected from the compounds of formula:
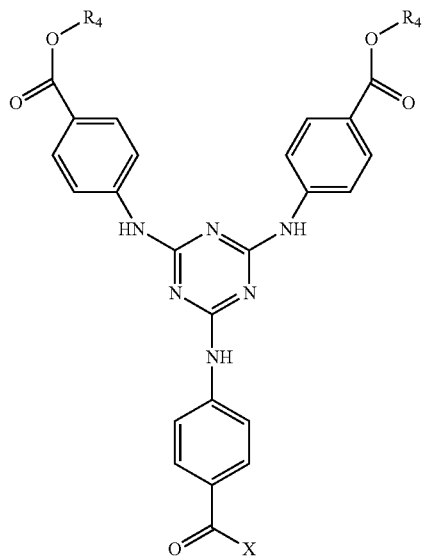
wherein X is as defined above and R4 is C1-C12 alkyl;
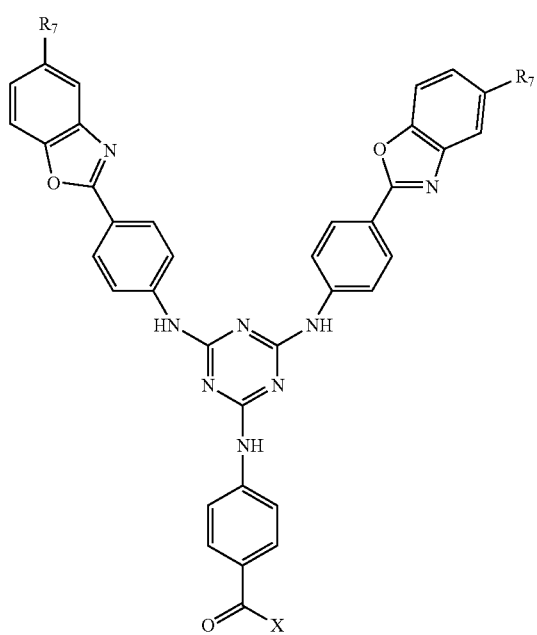
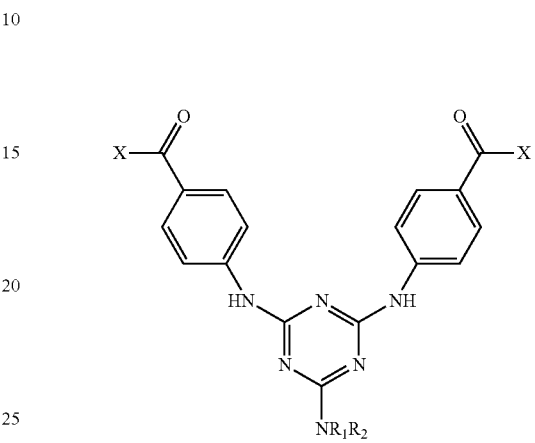
wherein X is as defined above, R7 are C1-C12 alkyl or isoalkyl groups;
wherein X is as defined above, R1 is hydrogen and R2 is alkyl or C1-C12 isoalkyl;
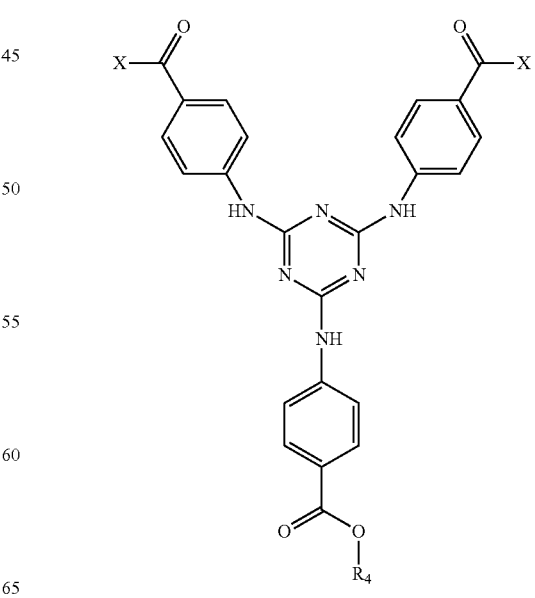

wherein X is as defined above, R4 is C1-C12 alkyl or isoalkyl;

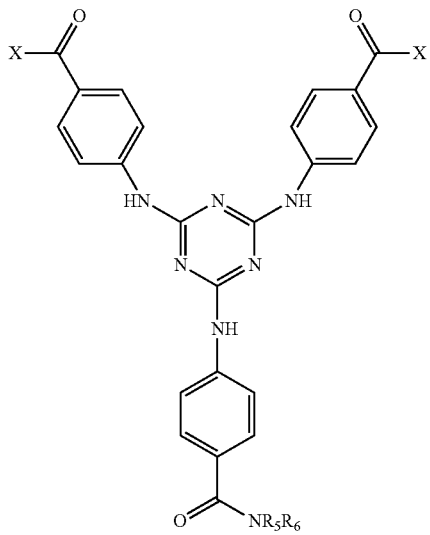

wherein X is as defined above, R5 is hydrogen, R6 is C1-C12 alkyl or isoalkyl.

8. A process for the preparation of the compound of formula I

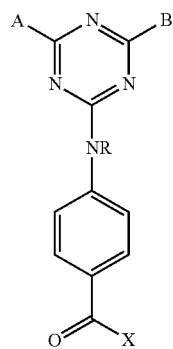

wherein A and B are defined in claim 1 and are not groups of formula V,

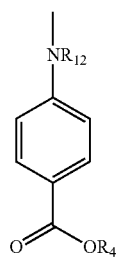

which comprises:

a) the reaction of cyanuryl chloride or bromide with one equivalent of a compound of formula

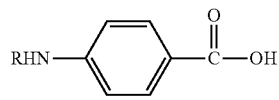

wherein R is defined in claim 1;

to give a compound of formula:

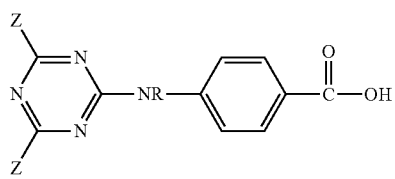

or a salt thereof, wherein Z is chlorine or bromine;

b) reaction of the resulting compound in a) with two equivalents of compounds of formula AH and/or BH wherein A and B are as defined above with the exclusion of the group of formula V, to give a compound of formula:

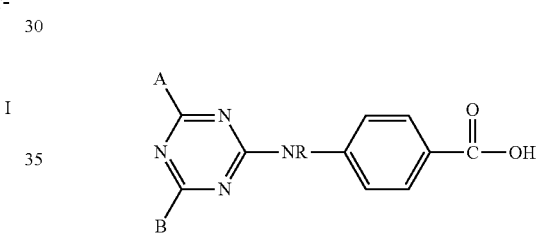

or a salt thereof;

c) reaction of the resulting compound in b) with halogenating agents.

9. A process according to claim 8 wherein step b) precedes step a).

10. A process for the preparation of the compound of formula I

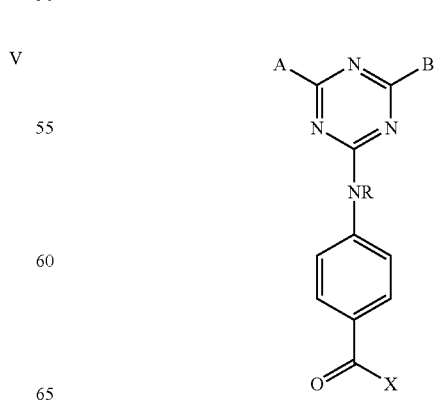

wherein A is not a group of formula V and B is a group of formula V,

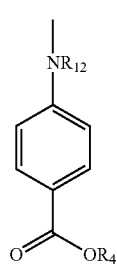

which comprises:

a) the reaction of cyanuryl chloride or bromide with an equivalent of a compound of formula AH to give a compound of formula:

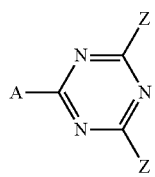

wherein Z is chlorine or bromine and A is as defined in claim 1;

b) reaction of the resulting compound in a) with two equivalents of a compound of formula

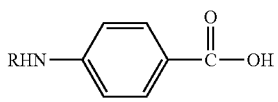

wherein R is as defined in claim 1;
to give a compound of formula:

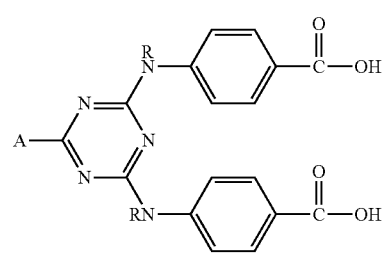

or a salt thereof;

c) reaction of the resulting compound in b) with halogenating agents.

11. A process according to claim 10 wherein step b) precedes step a).

12. Process for the preparation of a symmetrical triazine comprising reacting a compound of formula I

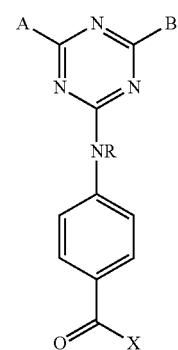

wherein A and B are as defined in claim 2
with an alcohol of formula R4-OH, an amine of formula-R5R6NH or an aminophenol of formula

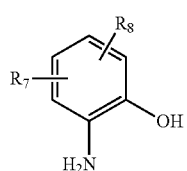

followed, in the latter case, by dehydration to form a benzoxazole ring, wherein R4, R5, R6, R7 and R8 are the same or different, and are hydrogen, straight or branched C1-C12 alkyl, C3-C6 cycloalkyl, R5 and R6, and together with the nitrogen atom they are linked to, can also form a morpholino ring; and R4, R5 and R6 can also be polyalkylene-polysiloxane groups.

13. Compound according to claim 6, wherein R4 is 2-ethylhexyl.

14. Compound according to claim 6, wherein when one of R5 or R6 is hydrogen the other is tert-butyl.

15. Compound according to claim 6, wherein when one of R7-R10 is hydrogen, the other is tert-amyl tert-amyl.
16. Compound according to claim 7 selected from the compounds of formula.
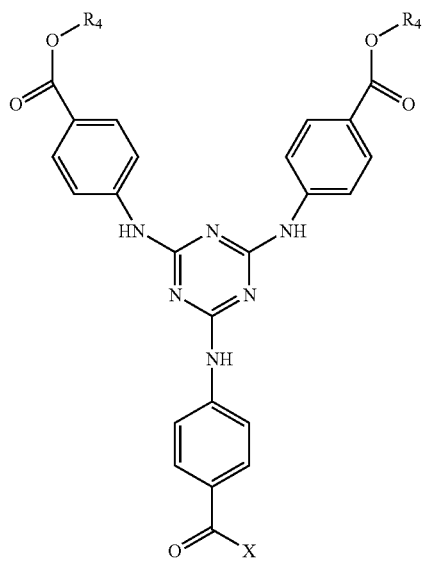
wherein X is chlorine and R4 is 2-ethylhexyl;
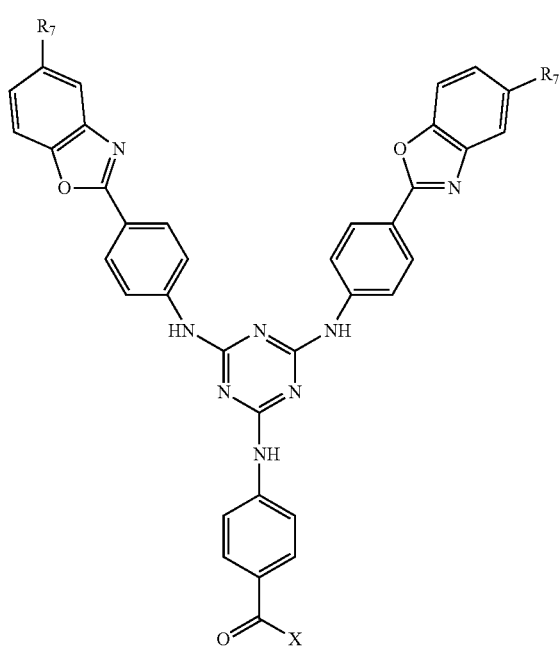
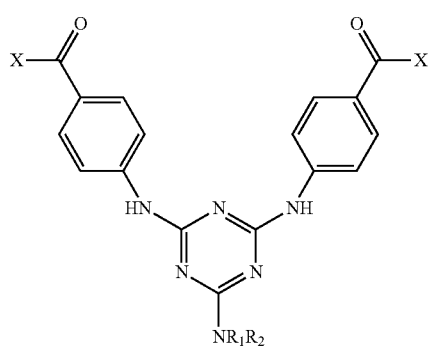
wherein X is chlorine and R7 are tert-amyl groups;
wherein R2 is 2-ethylhexyl and X is chlorine;
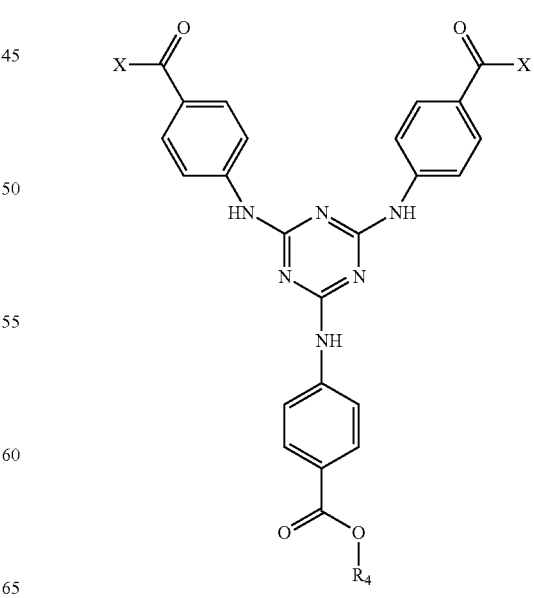

wherein R4 is 2-ethylhexyl and X is chlorine;
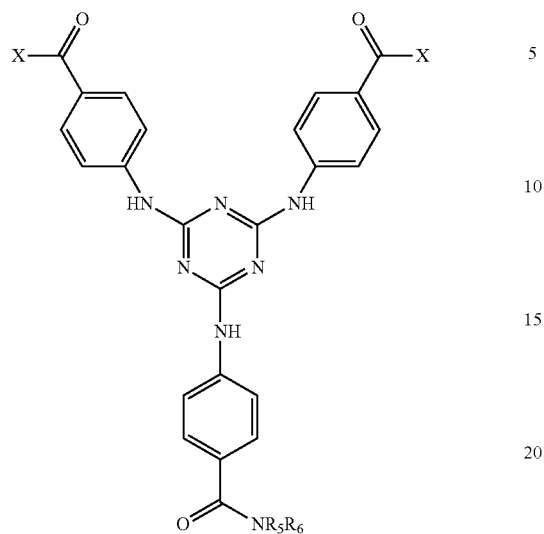
wherein R6 is tert-butyl and X is chlorine.
17. Compound of formula I according to claim 1, wherein R4, R5 and R6 are —$(CH_2)_n$-Sil, wherein Sil is a polysiloxane group.
* * * * *